United States Patent [19]

McAlister et al.

[11] Patent Number: 5,599,324
[45] Date of Patent: Feb. 4, 1997

[54] CATHETER FOR ADMINISTERING A LIQUID AGENT

[75] Inventors: Gary B. McAlister, Franklin; Roy H. Sullivan, III, Millville; Charles B. Warich, Milford, all of Mass.

[73] Assignee: Boston Scientific Corporation, Natick, Mass.

[21] Appl. No.: 434,242

[22] Filed: May 4, 1995

[51] Int. Cl.⁶ ............................................. A61M 25/00
[52] U.S. Cl. ........................... 604/280; 604/53; 604/283
[58] Field of Search .......................... 604/280–284, 604/53, 43, 264, 93, 272, 256, 164–169

[56] References Cited

U.S. PATENT DOCUMENTS

| | | | |
|---|---|---|---|
| 5,336,205 | 8/1994 | Zenzen et al. | 604/280 |
| 5,397,302 | 3/1995 | Weaver et al. | 604/54 |
| 5,472,417 | 12/1995 | Martin et al. | 604/43 |
| 5,486,159 | 1/1996 | Mahorkar | 604/280 |
| 5,507,732 | 4/1996 | McClure et al. | 604/280 |

*Primary Examiner*—John D. Yasko
*Attorney, Agent, or Firm*—Pearson & Pearson

[57] ABSTRACT

A catheter for the administration of a liquid agent at a target site includes a catheter tube, a handle and a conduit that extends through a central volume formed in the handle. The catheter includes a guidewire lumen and two parallel liquid agent transfer lumens. The conduit seals into the proximal end of the guidewire lumen and to the handle at a first entry port and spans the central volume. The tube therefore prevents the transfer of any liquid agent into the guidewire lumen and provides a passageway for enabling the catheter to transfer over the guidewire. With two transfer lumens the catheter tube provides a maximum transfer flow rate while maintaining the ability of the catheter to resist kinking and bending.

15 Claims, 2 Drawing Sheets

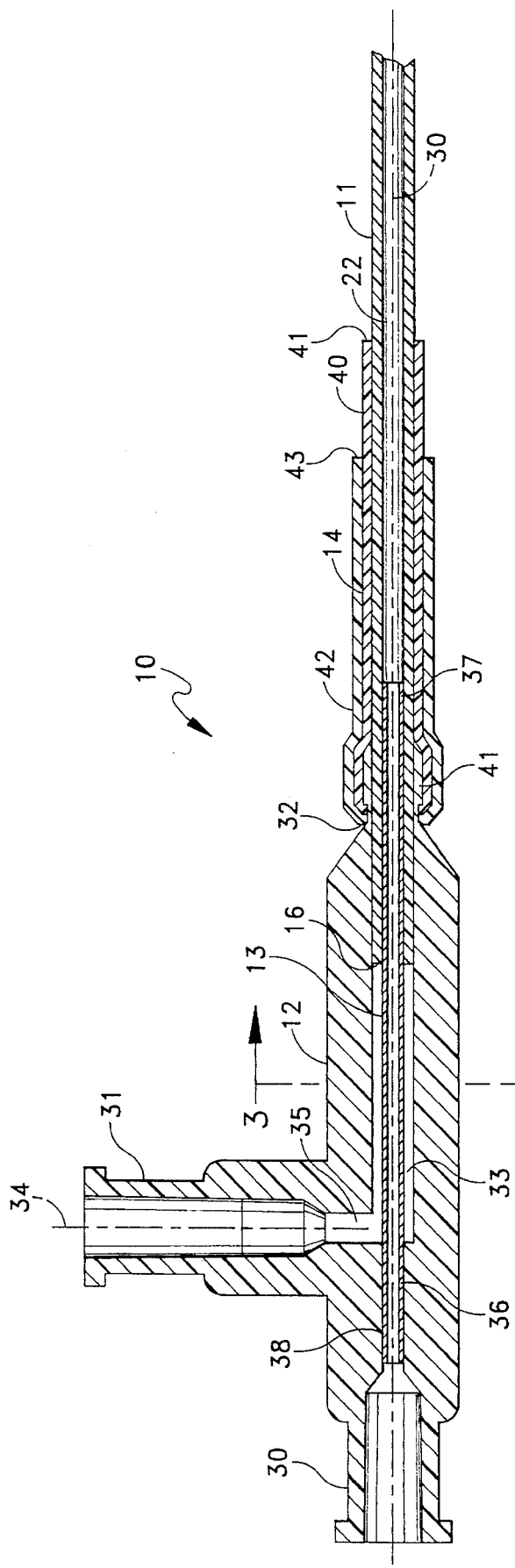
FIG. 2
FIG. 3
FIG. 4

5,599,324

CATHETER FOR ADMINISTERING A LIQUID AGENT

Background of the Invention

1. Field of the Invention

This invention generally relates to catheters for use in enabling the visualization of the anatomy and more specifically to catheters that are particularly adapted for the field of endoscopic retrograde cholangiopancreatography.

2. Description of Related Art

The use of catheter-like devices for administering therapeutic, diagnostic and vaso-occlusive agents at predetermined target sites in a patient is well known. Initially catheters of this type, particularly for use in the field of endoscopic retrograde cholangiopancreatography (ERCP) procedures, were constructed from Teflon® and included a single lumen sized to accommodate a wire guide and to act as a liquid agent transfer channel. As the ERCP catheters typically were also adapted to be inserted over guidewires or through working channels of endoscopes, they were typically shipped with a stylet wire in the lumen that would stiffen the catheter to prevent kinking or bending. The styler had to be removed prior to any use of the catheter with a guidewire or after the catheter was inserted through an endoscopic device.

The presence of a guidewire in the lumen may restrict the transfer of liquid agents, such as radiographic contrast agents, through the lumen past the guidewire. Consequently after a physician inserted the ERCP catheter, any guidewire would be removed to facilitate the administration of a radiopaque contrast agent to determine the location of various obstructions.

Often times it became necessary to reposition the catheter. This required the reinsertion of the guidewire through the lumen to enable catheter relocation. Then it was necessary to remove the guidewire again. The need to maintain sterile conditions further complicated this procedure especially as to the guidewire while it was removed from the catheter. Given the nature of the contrast agents, it was also found that in some cases the contrast agent, guidewire and lumen in combination can become stiff thereby reducing catheter flexibility. In some situations it was even possible for the guidewire to stick in the catheter thereby requiring the removal of both the catheter and the guidewire. Single lumen catheters also were characterized by back flow whereby the contrast agent could squirt back out the proximal end of the catheter and onto the administering medical professional.

More recently there have been introduced dual lumen ERCP catheters in which one of the lumens is adapted for receiving a guidewire or stylet and the other is adapted for transferring the contrast agent. The transfer lumen has typically either had a circular cross-section or crescent-shaped cross-section, the latter being disclosed, for example, in U.S. Pat. No. 5,397,302 to Weaver. In the Weaver patent a catheter formed of polyurethane or nylon has a durometer of about 60 D and a hydrophilic coating thereby to provide lubricity, kink resistance and suppleness. The catheter tube has substantially cylindrical side walls, a proximal end for connection to a source of contrast medium and a distal end for entry into the common biliary duct of a patient. The tube contains a first crescent-shaped liquid agent transfer lumen for transporting contrast media from the source of the contrast medium to the biliary duct. A second circular lumen facilitates the insertion of the catheter over a guidewire.

Although dual-lumen catheters of the prior art eliminate many of the handling problems posed by single lumen catheters, in terms of removing and reinserting a stylet or guidewire, several undesirable characteristics still exist. For example, dual lumen catheters for ERCP procedures are limited to a maximum overall diameter. The addition of a second lumen of sufficient size to provide adequate transfer rates through the catheter of that maximum size can weaken the catheter wall and subject the catheter to being burst while a contrast agent is being administered. Further, even if some minimum wall thickness is maintained to prevent bursting, a catheter being inserted through an endoscope without a guidewire is subject to kinking and bending under the axial pressure required to move the catheter relative to the endoscope. Kinking and bending have a real potential for damage to the catheter. Consequently physicians oftentimes will become quite deliberate and even tentative in advancing a catheter as the transfer force increases in order to avoid kinking or bending with the subsequent requirement that the catheter be withdrawn and destroyed. Consequently even dual lumen catheters typically include a stiffening stylet for use with endoscopic devices. Still further, these constraints on the size of the second lumen can, for reasonable pressures exerted on the liquid agent, limit flow rate through the lumen to an unacceptably low value.

SUMMARY

Therefore it is an object of this invention to provide a catheter for the administration of a liquid agent at a target site that is characterized by improved flow through the catheter.

Another object of this invention is to provide a catheter for the administration of a liquid agent at a target site that is characterized by improved flow through the catheter and by separation of the paths for the liquid agent and a guidewire.

Still another object of this invention is to provide a catheter for the administration of a liquid agent at a target site that can be led through an endoscopic device without the need for a stiffening stylet.

Yet another object of this invention is to provide a catheter for the administration of a liquid agent at a target site that can be led through an endoscopic device without buckling or kinking.

Still yet another object of this invention is to provide a catheter adapted for use in endoscopic retrograde cholangiopancreatography procedures that includes separate lumens for a guidewire and for the transfer of a contrast agent from a proximal site to a distal site.

In accordance with one aspect of this invention a catheter for the administration of a liquid agent at a target site within a patient comprises a catheter tube, a handle and a conduit. The catheter tube includes first, second and third lumens that extend through the catheter tube and exit through a proximal end and a distal end that is adapted for transit to a target site. The handle has first and second entry ports and a catheter port, each port extending between the exterior of the handle and a central volume. The proximal end of the catheter tube is affixed in the catheter port such liquid agent administered under pressure through the second port transfers through the second and third lumens in parallel to the distal end for ejection at the target site. The conduit extends through the central volume and has one end terminating at the first lumen at the proximal end of the catheter tube and the other end terminating in the first entry port thereby to prevent the transfer of liquid agent from the central volume into the first lumen.

In accordance with another aspect of this invention, an ERCP cannula for administering a contrast agent in the biliary tree comprises a catheter tube, a handle, a thin-walled tube and an outer seal. The catheter tube has a guidewire lumen and first and second transfer lumens formed between a proximal end and a distal end that is adapted for location in the biliary tree. The first and second transfer lumens have a combined area in cross-section of approximately 25% of the area in cross-section of the guidewire lumen. The handle includes a first entry port and a catheter port spaced along a first axis, a second entry port extending along a second axis that is transverse to the first axis and a central volume coextensive with portions of the first and second axes. The thin-walled tube extends along the first axis through the central volume. One end of the tube is sealed to the first entry port, and the other end of the tube is sealed against the catheter tube in the guidewire lumen. The outer seal is formed about portions of the exterior of the handle at the catheter port and portions of the exterior of the catheter extending from the catheter tube.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 2 is a view, in cross-section, of a portion of the catheter shown in FIG. 1;

FIG. 3 is a view, in cross-section, taken along lines 3—3 in FIG. 2; and

FIG. 4 is an enlarged view, in cross-section, taken along lines 4—4 in FIG. 1.

DESCRIPTION OF ILLUSTRATIVE EMBODIMENTS

Figure 1:
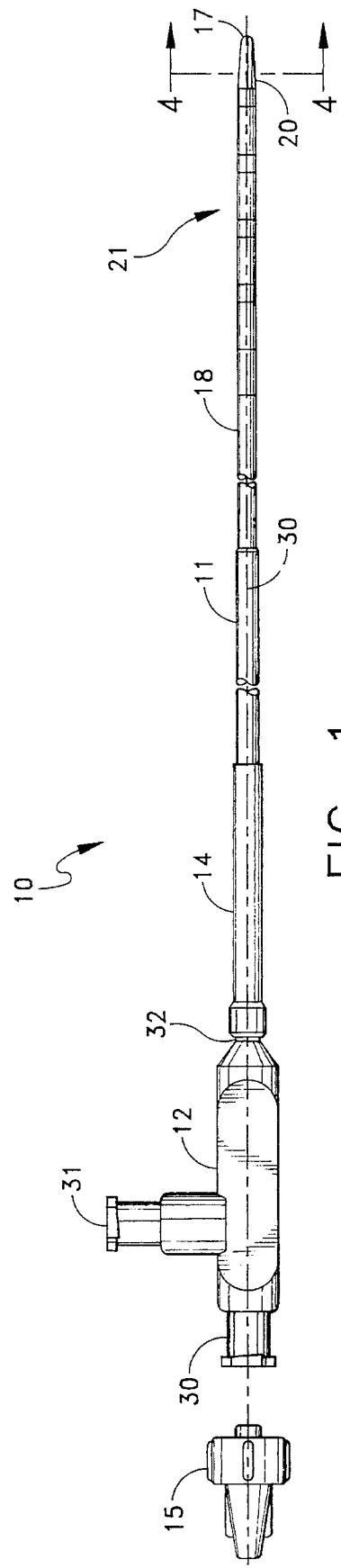
FIG. 1 is a plan view of a catheter constructed in accordance with this invention.

As shown particularly in FIGS. 1 and 2, a catheter 10 for the administration of a liquid agent at a target site within a patient includes a catheter tube 11, a handle 12, a conduit 13, a seal 14 and an end cap 15. The catheter tube 11 extends between a proximal end 16 and a distal end 17. A section 18 of the catheter tube 11 adjacent the distal end 17 has a reduced diameter that terminates in a tapered tip portion 20. The reduced diameter section 18 carries a series of visual and radiographic markers 21. The reduction of the catheter tube diameter, the taper of the distal tip 20 and utilization of such radiographic markers 21 is well known in the art.

FIG. 3 depicts the construction of the catheter tube in accordance with this invention looking at the proximal end 16 while FIG. 4 depicts a cross-section through the tapered tip 20. The tube 11 can be formed of TFE or other known biocompatible materials useful in catheter construction. Typically the catheter tube 11 is extruded according to known methods to produce three lumens that exit through the proximal end 16 and the distal end 17. A first lumen 22 accommodates a guidewire. A second lumen 23 and third lumen 24 act a liquid transfer conduits for conveying a contrast or other liquid agent from the handle 12 in FIG. 1 to the distal end 17.

For ERCP cannula applications, the catheter tube 11 may have a diameter of about 0.10". In such an embodiment the first lumen has a diameter at the proximal end of about 0.039" to accommodate a standard 0.035"guidewire. Each of the lumens 23 and 24 has a diameter of about 0.020". Approximately 75% of a solid cylinder having the diameter of the catheter 11 remains after the extrusion of the three lumens 22 through 24.

Referring to FIG. 4, the material remaining after forming the first lumen 22 and the second and third lumens 23 and 24 defines an outer ring 25 denoted generally by a dashed line and three interconnected, generally radially extending ribs designated by reference numerals 26, 27 and 28. The ribs 26 through 28 and the outer ring 25 form a column structure that resists kinking and bending when axial thrust is applied to the catheter tube 11 such as thrust along the axis 30 shown in FIGS. 1 and 2. It has been found that a catheter 10 with this catheter tube structure can be led through the working channel of an endoscope without kinking or bending and without the addition of a stylet. Thus a styler can be eliminated to simplify the use of and reduce the cost of the catheter 10.

As is known, after the extrusion of the tube 11 forming the lumens 22 through 24, the reduced diameter portion 18 and tapered tip portion 20 are formed by drawing the corresponding portions of the catheter tube 11 through a reducing die with mandrels located in each lumen. Consequently any reduction in the overall diameter need not significantly reduce the size of any lumens, so the lumen 22, for example, still accommodates a standard guidewire. Thus, in accordance with this construction, each of the lumens 22 through 24 exits through the distal end 17 of the catheter device 11 and provides a passage 22 for the guidewire and two passages 23 and 24 for the administration of a contrast agent.

Referring now to FIGS. 1 and 2, the handle 12 includes a first entry port 30, a second entry port 31, a catheter port 32 and an internal central volume or chamber 33. Both the first and second entry ports form conventional portions of Leur lock fittings. Referring specifically to FIG. 2, the central volume 33 has a generally cylindrical shape lying along the extension of the catheter axis 30. The first entry port 30 and the catheter port 32 are coaxial with the axis 30. A portion of the catheter tube 11 adjacent the proximal end 16 lies in the catheter port 32 with the outer surface of the catheter tube 17 being sealed to the portions of the handle 12 forming the catheter port 32.

Still referring to FIGS. 2 and 3, there is also included in the handle 12 a conduit 36 in the form of a thin-walled stainless steel tube, or "hypotube". One end portion 37 of the conduit 36 extends into the first lumen 22 and produces a seal between the outer surface of the conduit 36 and the inner surface of the catheter tube 11 forming the lumen 22. The other end portion 38 of the tube 36 is sealed to the handle 12 at the entry port 30. The volume of the chamber 33 is selected so that the total cross-sectional area of the central volume 33 minus the area of the tube 36 is at least as great as the combined areas of the lumens 22 and 24.

The second entry port 31 lies along an axis 34 that extends at right angles to the axis 33. The port 31 provides access to the central volume through a transverse passage 35.

As will now be apparent, the tube 36, that is coaxial with the axis 30, provides an isolated path for a guidewire that extends from the first port 30 through the tube 36 and the first lumen 22. As contrast agent is administered through the second entry port 34 under pressure, it transfers through the passage 35 into the central volume 33 around the tube 36.

Given the seal between the tube 36 and the catheter tube 11, this material can not enter the lumen 22, but instead flows only through the lumens 23 and 24 to be ejected at the distal end 17 as shown in FIG. 1.

When a physician uses the catheter 10 in a procedure requiring a guidewire, a physician first positions the guidewire in the patient and then threads the distal tip 17 over the proximal end of the guidewire such that the guidewire travels through the lumen 22 and the distal tip 20 moves to a target site. The radiographic markers 21 provide a means for determining the position of the distal tip 17 during the location process.

Without removing the guidewire, the physician then can attach a syringe or other device to the second entry port 31 and force a contrast agent through the passage 35, the central volume 33 and the lumens 23 and 24 in parallel to be discharged where the lumens 23 and 24 exit the distal end 17. The seals formed between the tube 36 and the handle 12 and between the tube 36 and the catheter tube 11 around the guidewire 22 assure isolation of the guidewire lumen 22. Thus if it is necessary to relocate the distal tip 20, there is no need to remove the guidewire.

When the guidewire is in place, the free volume around the guidewire 22 in the lumen 22 is sufficiently small that any transfer of contrast agent back through the lumen 22 as it is discharged from the distal end 17 is blocked. When the catheter 10 shown in FIG. 1 is used with an endoscopic device and without a guidewire, the lumen 22 constitutes a path of low flow resistance to the contrast agent as it exits the distal end 17 through the lumens 23 and 24. In such procedures, the end cap 15 can be attached to the first entry port 30 effectively sealing the lumen 22. The end cap 15 is a typical Luer lock end cap as known in the art. Should any contrast agent begin to enter the lumen 22 at the distal end 17, any air in the lumen 22 will compress and eventually reach an equilibrium pressure whereby further displacement along the lumen 22 will not occur. Thus, the use of the end cap 15 overcomes the prior art problem of having contrast agent flowing back through the lumen 22 onto the personnel administering the fluid.

Referring again to FIGS. 1 and 2, one particular embodiment of the seal 14 comprises a two-part structure with each part being formed of a heat shrinkable material such as polyolefin. A first seal 40 is formed onto a circumferential band 41 formed integrally with the handle 12 at the catheter port 32 to improve a mechanical grip with the seal 40. The remaining portion of the seal 40 extends distally along the outer surface of the catheter tube 11 for some predetermined distance to an end 41. A second heat shrinkable tube 42 can be applied over the first tube 40 to terminate at an end 43 such that a small portion of the tube 40 is exposed distally of the end 43. In a preferred embodiment, the two tubes are formed of different colors so the exposed portion of the tube 40 provides a marking function for facilitating measurements during an ERCP procedure.

Therefore in accordance with the various aspects of this invention, there has been disclosed a catheter for the administration of liquid agents at a target site in a patient, particularly contrast agents for use in ERCP procedures, that includes a three-lumen catheter tube, a handle and a thin-walled tube that is sealed in the proximal end of a guidewire lumen in the catheter tube. The proximal end of the catheter tube and the thin-walled tube extending from the catheter tube are inserted into a catheter port of a handle with the other end of the thin-walled tube being sealed to the handle at a first entry port thereby to provide passage for a standard guidewire through the first entry port the tube and the first lumen. A second entry port also communicates with the central chamber to provide a path for contrast agent through the central volume and second and third lumens to the distal end through the catheter tube. The combination of the thin-walled tube and the central volume isolate the guidewire lumen from the liquid transfer lumens thereby to prevent the transfer of contrast agent into the guidewire lumen so that a guidewire operates freely even during repeated operations.

This structure eliminates the steps of removing a guidewire during successive operations because there is a separate path for the contrast agent. When the catheter is used in endoscopic devices, its cross-section enables the catheter to be inserted through the endoscope working channel without a styler.

This invention has been described in terms of a particular embodiment in which the various components of the catheter have specific configurations and dimensions and are composed of particular materials. It will be apparent that this invention could be embodied in alternative structures and having different dimensions and formed of different materials. For example, the thin-walled tube that isolates the guidewire lumen from the remaining lumens is shown along a straight axis, this axis might be formed within an angular offset if desired. Therefore, it is the intent of the appended claims to cover all such variations and modifications as come within the true spirit and scope of this invention.

What is claimed as new and desired to be secured by Letters Patent of the United States is:

1. A catheter for the administration of a liquid agent at a target site within a patient comprising:

(A) a catheter tube terminating in proximal and distal ends and having first, second and third lumens extending therethrough and exiting through the proximal and distal ends, said distal end being adapted for location at the target site, (B) a handle having a central volume and first and second entry ports and a catheter port extending between the exterior of said handle and said central volume, the proximal end of said catheter tube being affixed in said catheter port whereby liquid agent administered through said second port to said central volume transfers through said second and third lumens to the distal end for ejection at the target site, (C) a conduit extending through said central volume and having one end terminating in said first lumen at the proximal end of said catheter tube and the other end terminating in said first entry port thereby to prevent the transfer of liquid agent from said central volume into said first lumen.

2. A catheter for the administration of a liquid agent as recited in claim 1 wherein said conduit is a thin-walled tube.

3. A catheter for the administration of a liquid agent as recited in claim 2 wherein said thin-walled tube is formed of stainless steel.

4. A catheter for the administration of a liquid agent as recited in claim 2 wherein the area of said first lumen in cross section exceeds the area in cross section of each of said second and third lumens.

5. A catheter for the administration of a liquid agent as recited in claim 4 wherein each of said first, second and third lumens is circular in cross section.

6. A catheter for the administration of a liquid agent as recited in claim 5 wherein said first lumen is sized to receive a medical guidewire and said second and third lumens collective have an area in cross section that is approximately 25% of the area of said first lumen in cross section.

7. A catheter for the administration of a liquid agent as recited in claim 2 wherein said first entry port and said catheter port are spaced along a first axis and wherein said thin-walled tube is coaxial with the first axis and said second entry port extends along a second axis transverse to the first axis.

8. A catheter for the administration of a liquid agent as recited in claim 7 additionally comprising gripping means formed on the exterior of said handle for facilitating the use of said catheter.

9. A catheter for the administration of a liquid agent as recited in claim 8 wherein the first and second entry port axes define a plane and said gripping means comprises spaced planar portions formed integrally with said handle in parallel with and spaced from the plane defined by the entry port axes.

10. An ERCP cannula for administering a contrast agent in the biliary tree within a patient comprising:

(A) a catheter tube terminating in proximal and distal ends and having a guidewire lumen and first and second transfer lumens formed between the proximal and distal ends, (B) a handle with a first entry port and a catheter port spaced along a first axis, a second entry port extending along a second axis that is transverse to the first axis and a central volume coextensive with portions of the first and second axes, (C) a thin-walled tube extending along the first axis through said central volume, one end of said tube being sealed to said first entry port and the other end of said tube being located in the guidewire lumen of said catheter tube in a sealed relationship with said catheter tube, and (D) an outer seal formed about portions of the exterior of said handle at said catheter port and about portions of the exterior of catheter tube extending from said handle adjacent thereto.

11. An ERCP cannula for the administration of a contrast agent in the biliary tree as recited in claim 10 wherein said catheter tube comprises an extruded TFE material, said handle is formed of molded nylon and said thin-walled tube is composed of stainless steel.

12. An ERCP cannula for the administration of a contrast agent in the biliary tree as recited in claim 11 wherein said outer seal comprises a heat-shrinkable material.

13. An ERCP cannula for the administration of a contrast agent in the biliary tree as recited in claim 11 wherein said catheter tube is tapered at the distal end and wherein said lumens are tapered correspondingly.

14. An ERCP cannula for the administration of a contrast agent in the biliary tree as recited in claim 11 additionally comprising spaced markers adjacent the distal end of said catheter tube.

15. An ERCP cannula for the administration of a contrast agent in the biliary tree as recited in claim 11 additionally comprising an end cap for closing said first entry port, said first entry port including means for securing said end cap to said handle.

* * * * *